United States Patent [19]
Phillips

[11] Patent Number: 5,460,056
[45] Date of Patent: Oct. 24, 1995

[54] UNDERWATER SAMPLING APPARATUS

[75] Inventor: William H. Phillips, Saginaw, Mich.

[73] Assignee: Trippensee Corporation, Saginaw, Mich.

[21] Appl. No.: 236,271

[22] Filed: May 2, 1994

[51] Int. Cl.[6] .................................................. G01N 1/12
[52] U.S. Cl. .................................................. 73/864.66
[58] Field of Search ........................... 73/864.65–864.67

[56] References Cited

U.S. PATENT DOCUMENTS 3,949,497  4/1976  Crump .
4,846,004  7/1989  Richards et al. ................. 73/864.67

FOREIGN PATENT DOCUMENTS 0527628  9/1976  U.S.S.R. ........................... 73/864.66
0562747  6/1977  U.S.S.R. ........................... 73/864.66
0744267  6/1980  U.S.S.R. ........................... 73/864.66
1326941  7/1987  U.S.S.R. ........................... 73/864.66

*Primary Examiner*—Robert Raevis
*Attorney, Agent, or Firm*—Learman & McCulloch

[57] ABSTRACT

Sampling apparatus for taking underwater samples has an open ended tube fitted with closures biased for movement from positions in which the ends of the tube are open to a position in which the ends of the tube are closed. A releasable latch releasably maintains the closures in their open positions. A latch release line is coupled to the latch for transmitting to the latch from a remote point a tensile force of such magnitude as to release the latch. An elastic connector acts on the closures in response to release of the latch to move the closures to their closed positions.

11 Claims, 2 Drawing Sheets

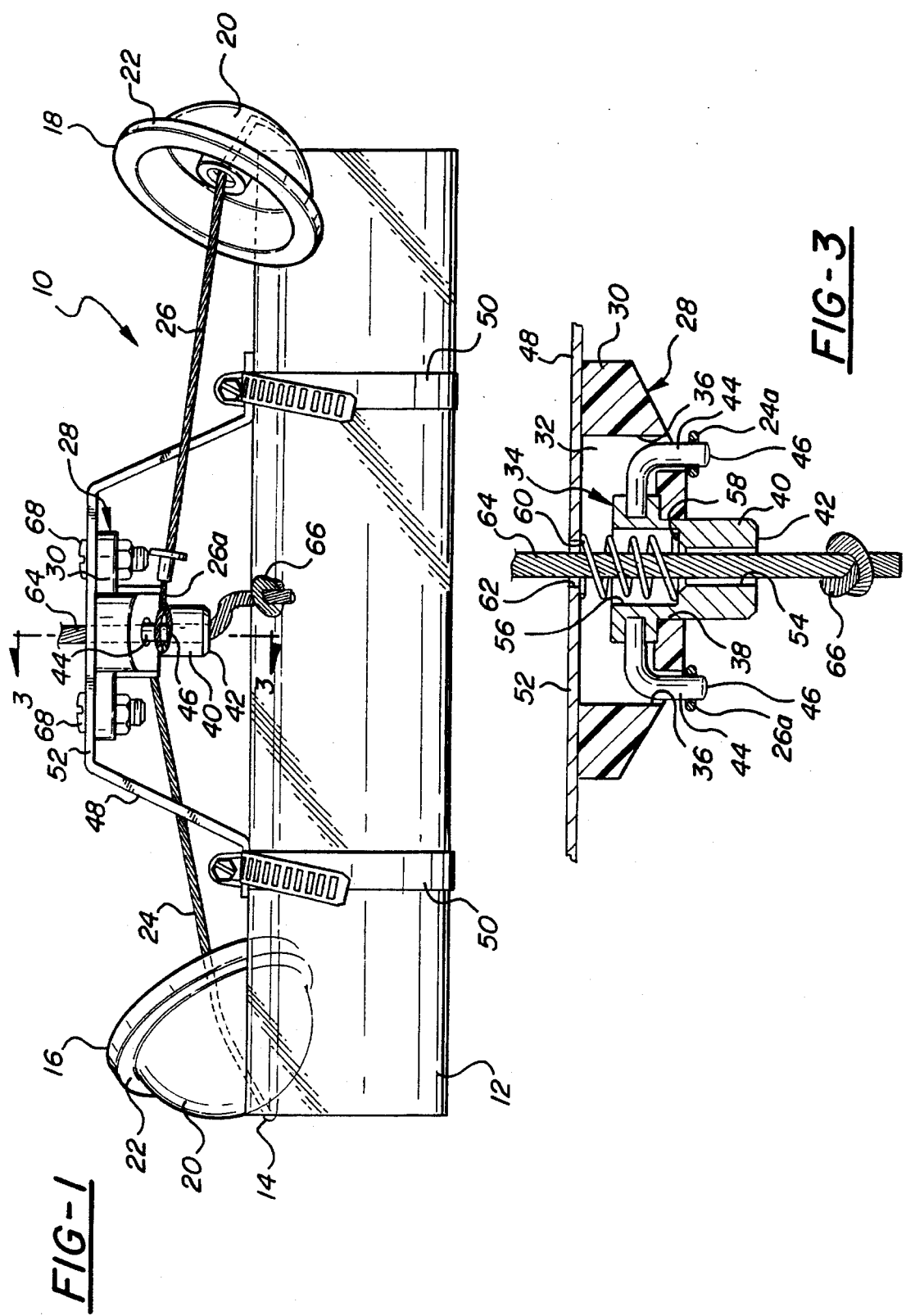

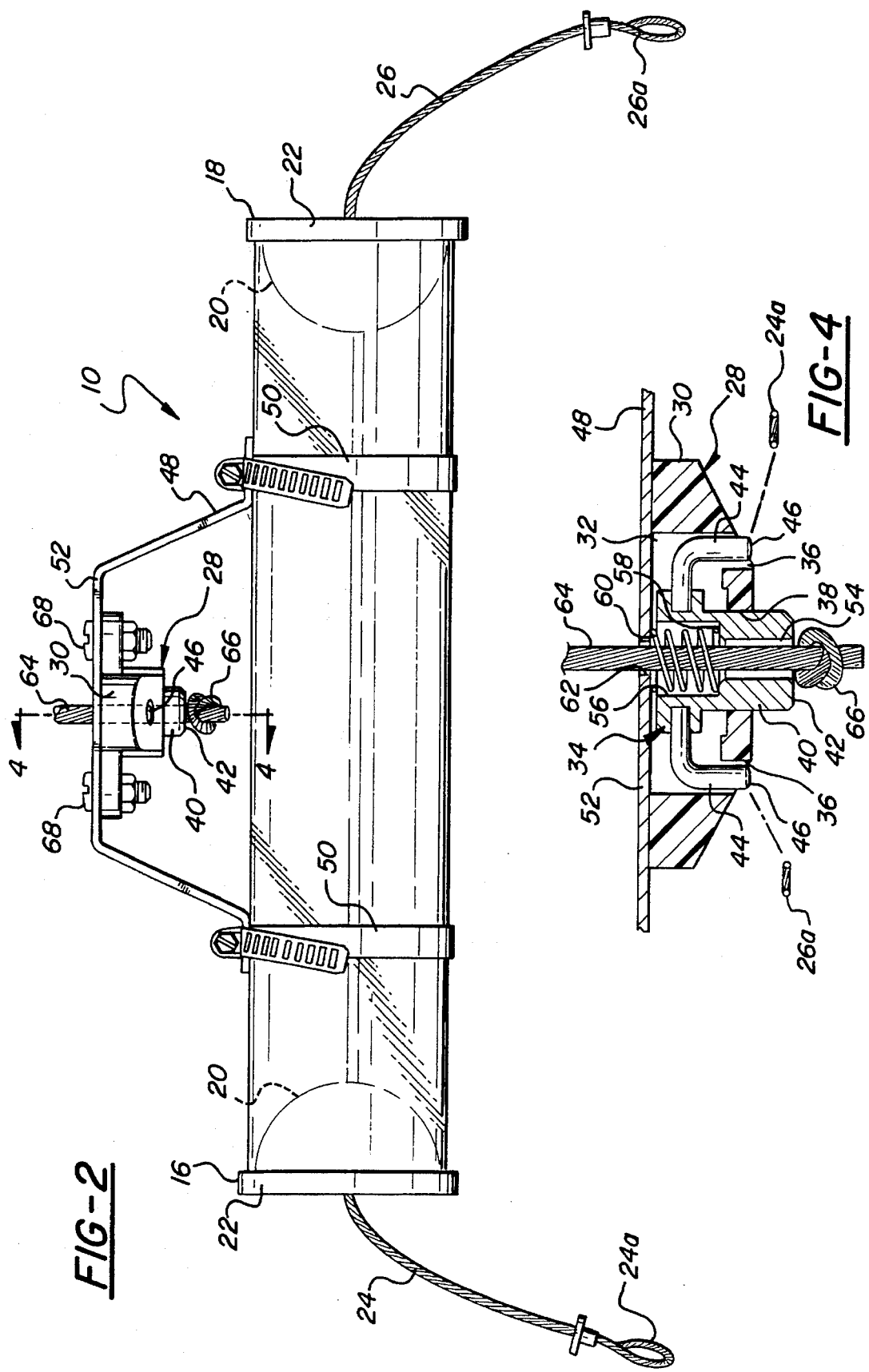

5,460,056

UNDERWATER SAMPLING APPARATUS

This invention relates to underwater sampling apparatus having a normally open container adapted to be submerged in a body of water whereupon the container may be closed to entrap in the container an underwater sample.

BACKGROUND OF THE INVENTION

For some limnological and oceanographic studies it is important that underwater samples be taken and that such samples be protected against dilution or modification due to leakage of the sampler during retrieval of the latter. One type of sampler designed for this purpose comprises a hollow tube, normally open at both ends, and having end closures or stoppers which are adapted to be moved from open positions to sealing positions in response to the dropping of a weighted messenger along the line or cable which supports the sampler. The stoppers are latched in their open positions via a latch which has a release mechanism that is tripped by compressive force generated by the weighted messenger to enable the stoppers to move to their closed positions. Such a latch mechanism is disclosed in U.S. Pat. No. 3,949,497, granted Apr. 13, 1976.

Although commercially successful, this latch mechanism has its limitations, particularly in those instances in which the support line is inclined to the vertical at such an angle as to prevent downward movement of the weighted messenger at a rate of speed to strike the release mechanism with a force sufficient to trigger the release mechanism.

Because of the necessity of maintaining the support line in a position in which the messenger may travel downward at the necessary speed to actuate the release mechanism, conventional samplers may not be used in those instances in which high currents cause the sampler support line to assume an adverse angle to the vertical.

SUMMARY OF THE INVENTION

Sampling apparatus constructed according to the invention comprises a hollow container having at least one opening and a corresponding number of closure members biased to move from open positions to closed positions. A latch mechanism releasably holds the closure members in their open positions and is provided with a release actuator operable from a remote point to disable the latch and release the closure members. A line is coupled to the release actuator in such manner as to tether and support the container at a selected submerged depth and operate the actuator in response to application of tensile force on the line exceeding a predetermined threshold value to effect release of the latch mechanism and movement of the closure members to their closed positions, and regardless of the inclination of the support line.

The construction is such that the operator may effect closing of the container remotely therefrom simply by giving a sharp tug on the support line to trip the release actuator. This arrangement eliminates the need for a weighted messenger at all and permits the taking of underwater samples from shore simply by casting the container into the body of water, allowing it to descend to the desired depth, giving a sharp pull on the release line to trigger the release actuator, and thereby close the container for retrieval of the sample.

BRIEF DESCRIPTION OF THE DRAWINGS

FIG. 1 is a fragmentary elevational view of a water sampler constructed in accordance with the invention, the closures of the sampler being latched in open positions;

FIG. 2 is a view similar to FIG. 1 but illustrating the closures in closed positions;

FIG. 3 is an enlarged sectional view taken on the line 3—3 of FIG. 1; and

FIG. 4 is an enlarged sectional view taken on the line 4—4 of FIG. 2.

DETAILED DESCRIPTION

Sampling apparatus constructed according to a presently preferred embodiment of the invention is designated generally at 10 in the drawings and comprises a hollow, tubular sampling body or container 12 open at least at one end and preferably at both ends. An elastic connecting member 14, preferably surgical tubing, extends through the container 12 and is fixed at its opposite ends to identical closure members 16 and 18. The closure members 16 and 18 are formed of rubber or rubbery material and each has a hemispherical hollow body 20 dimensioned to be received with a sealed fit into the adjacent open end of the container 12. Each closure also has an enlarged base flange 22 dimensioned to seat on the end face of the container 12, as illustrated in FIG. 2, to seal the container end.

One end of an inelastic cable 24 forming part of a releasable latch mechanism is secured to the closure member 16 and a similar cable 26 is secured to the closure member 18. The cables 24, 26 terminate at their other ends in retaining loops 24a, 26a, the purpose of which will be explained subsequently.

The preferred latch mechanism is indicated generally by the reference numeral 28 and may be of the same construction as that disclosed in the aforementioned patent and to which reference may be had for a more detailed disclosure. Briefly, however, the latch mechanism 28 comprises a body 30 having a cavity 32 in which a latch member 34 is accommodated. The body 30 has a pair of laterally spaced openings 36 which flank a larger, intermediate opening 38, all of such openings communicating with the cavity. The latch member 34 has a release actuator or plunger 40 slideably fitted in the intermediate opening 38 and having a free end provided with a flat end face 42. Slideably accommodated in each of the openings 36 is a latch retainer pin 44 having a smoothly rounded nose 46 at its free end and coupled at its opposite end to the release actuator 40 for conjoint movement therewith.

A generally U-shaped mounting bracket or strap 48 is secured at its opposite ends to the container 12 by clamps 50 which encircle the container. A central portion 52 of the bracket 48 is spaced laterally from the container by an amount sufficient to facilitate the mounting of the latch mechanism 28 at the underside of the bracket portion 52 so that the actuator 40 and the latch pins 44 project toward container 12 with their free ends 42 and 46 spaced from the container. The orientation of the latch parts 40 and 44 is reversed from that of the corresponding parts of the mechanism shown in the patent.

The actuator plunger 40 has a bore 54 which communicates with a counterbore 56, the juncture of the bore and counterbore forming a shoulder 58 between the ends of the plunger. Accommodated within the bore 54 is a compression spring 60 one end of which seats upon the shoulder 58 and the opposite end of which seats upon the underside of the central portion 52 of the bracket 48. The spring 60 acts to urge the release actuator 40 and the latch pins 44 constantly in a direction outwardly of the body 30 and toward the container 12. The bracket 48 has an aperture 62 aligned with the bore 54 in the actuator 40. The lower end of a combined tether or support and latch operating line 64 is threaded through the aperture 62 and bore 54 and provided with a stop or enlargement 66 of such size as to be incapable of passing through the bore 54, thereby effectively coupling the line 64 to the release actuator 40.

The release actuator 40 and the pins 44 normally occupy the projected positions as shown in FIGS. 1 and 3 in which the actuator 40 and the latch pins 44 protrude beyond the body 30. The combined tether and operating line 64 extends through the aperture 62 of the mounting bracket 48, through the spring 60, and through the counterbore 56 and bore 54 so that the enlargement 66 confronts and bears upon the end face 44 of the actuator 40.

When it is desired to take a sample, the closure members 16 and 18 are moved bodily to their open positions by stretching the elastic connecting member 14 and latched in such positions by accommodating the latch pins 44 in the anchor loops 24a and 26a as illustrated in FIG. 1. The apparatus then may be lowered or cast into the body of water and allowed to descend to the desired depth to allow water at that depth to fill the container. The container will be supported at the desired depth by the line 64.

To obtain a sample the operator may apply a sharp, tensile force on the line 64 so as to cause the enlargement 66 to bear against the plunger 44 with a force sufficient to overcome the opposing force of the spring 60, thereby causing the plunger 40 and the pins 44 to be retracted into the cavity 32. As the pins 44 are retracted the anchor loops 24a and 26a of the cables are stripped off the latch pins 44, thereby enabling the elastic connecting member 14 to return the closure members 16 and 18 automatically to their closed positions as illustrated in FIG. 2. The sample thus is accommodated within the container which has its ends sealed by the closures. The apparatus may then be retrieved by means of the line 64.

As has been mentioned, the sampler may be cast into the water from the shore in those instances in which a boat or raft may not be available. Because the pins 44 are on opposite sides of the axis of movement of the actuator 40 relative to the container, and because the loops 24a and 26a are similarly positioned when they are coupled to the pins, the elastic member 14 tends to rock the pins about the axis of the actuator, thereby causing the sides of the pins to bear against the sides of the respective openings 36 and apply a frictional force on the pins resisting their retraction into the chamber. This minimizes any tendency on the part of the latch mechanism to release the closures prematurely during movement of the sampler.

Since release of the latch mechanism does not depend in any way upon the movement of a weighted messenger into engagement with the release actuator, the line 64 can assume any angle to the vertical without adversely affecting the release of the latch.

Although the disclosure of the invention has been concerned primarily with the taking of water samples, it is not limited to that use. For example, the latching apparatus disclosed herein may be used with dredges of the kind shown in U.S. Pat. No. 3,949,497.

The disclosed embodiment is representative of the preferred form of the invention, but is intended to be illustrative rather than definitive thereof. The invention is defined in the claims.

I claim:

1. Underwater sampling apparatus comprising:

a tubular container open at its opposite ends;

a first closure member for closing one end of said container and a second closure member for closing the other end of said container;

a connecting member interconnecting said closure members and biasing said closure members toward their closed positions;

a latch mechanism;

retaining means reacting between said latch mechanism and each of said closure members for releasably maintaining said closure members in open positions in which a sample freely may enter said container;

release actuator means operable to disable said latch mechanism;

and combined tethering and operating means coupled to said release actuator means for supporting said container at a selected submerged level and disabling said latch mechanism to effect disengagement of said retaining means in response to the application of tensile force on said tethering and operating means in excess of a predetermined threshold value.

2. The apparatus of claim 1 wherein said latch mechanism includes biasing means for yieldably urging said release actuator means constantly in one direction.

3. The apparatus of claim 2 wherein said latch mechanism extends longitudinally of said container and said biasing means urges said actuator means in a direction transversely of said container.

4. The apparatus of claim 1 wherein said connecting member comprises an elastic cord accommodated within said container and joined at opposite ends to said closure members.

5. Sampling apparatus according to claim 1 wherein said latch mechanism and said release actuator means are carried by said container substantially midway between its opposite ends to enable said container to assume a substantially horizontal position at said submerged level.

6. Sampling apparatus comprising:

a tubular container open at its opposite ends;

a first closure member for closing one end of said container and a second closure member for closing the other end of said container;

an elastic connecting member extending through said container and joined at its opposite ends to said first and second closure members and constantly urging said closure members toward their closed positions, said connecting member enabling said closure members to move to open positions in which said closure members are free from said ends of said container;

a latch mechanism for releasably holding said closure members in said open positions;

a release actuator operable to disable said latch mechanism and release said closure members; and a combined tether and release line coupled to said release actuator for supporting said container at a selected submerged level and actuating said release actuator in response to application of tensile force on said line in excess of a predetermined threshold value thereby to disable said latch mechanism and enable said connecting member to move said closure members to said closed positions.

7. Sampling apparatus comprising a hollow body having a chamber in communication with at least one opening through which a sample may enter said chamber; closure means movable between a first position in which said opening is open and a second position in which said closure means closes said opening; releasable latch means cooperable with said closure means for latching the latter in said first position; latch release means for releasing said latch means; combined tethering and operating means coupled to said latch release means for supporting said container at a selected submerged level and being operable to release said latch means in response to the application of tensile force in excess of a threshold value to said latch release means; and means responsive to the release of said latch means for moving said closure means to said second position.

8. Sampling apparatus according to claim 7 wherein the means responsive to the release of said latch means is elastic.

9. Sampling apparatus according to claim 7 wherein said body is tubular and open at its opposite ends.

10. Sampling apparatus according to claim 9 including one of said closure means at each end of said body.

11. Sampling apparatus according to claim 7 wherein said combined tethering and latch operating means comprises a line adapted to be held at a point remote from said body and operable to transmit said tensile force to said latch release means from said remote point.

* * * * *